United States Patent
Bonassa et al.

(10) Patent No.: US 9,839,760 B2
(45) Date of Patent: Dec. 12, 2017

(54) METHODS FOR CONTROLLING MECHANICAL LUNG VENTILATION

(71) Applicant: CareFusion 2200, Inc., San Diego, CA (US)

(72) Inventors: Jorge Bonassa, São Paulo (BR); Adriano De Lima Santos, São Paulo (BR); José Augusto Calvo Lonardoni, Itapevi (BR); Tito Coutinho Melco, São Paulo (BR)

(73) Assignee: VYAIRE MEDICAL CAPITAL LLC, Yorba Linda, CA (US)

( * ) Notice: Subject to any disclaimer, the term of this patent is extended or adjusted under 35 U.S.C. 154(b) by 417 days.

(21) Appl. No.: 14/251,494

(22) Filed: Apr. 11, 2014

(65) Prior Publication Data

US 2015/0290408 A1    Oct. 15, 2015

(51) Int. Cl.
  *A61M 16/00* (2006.01)
  *A62B 7/00* (2006.01)
  (Continued)

(52) U.S. Cl.
  CPC ...... *A61M 16/205* (2014.02); *A61M 16/0051* (2013.01); *A61M 16/204* (2014.02);
  (Continued)

(58) Field of Classification Search
  CPC ............... A61M 16/00–16/0012; A61M 16/005–16/0084; A61M 16/0096;
  (Continued)

(56) References Cited

U.S. PATENT DOCUMENTS

| 4,773,411 A | 9/1988 | Downs |
| 5,107,830 A | 4/1992 | Younes |

(Continued)

FOREIGN PATENT DOCUMENTS

| WO | WO-2009039525 A2 | 3/2009 |
| WO | WO-2011089491 A1 | 7/2011 |

(Continued)

OTHER PUBLICATIONS

International Search Report and Written Opinion for Application No. PCT/US2015/021589, dated Jun. 9, 2015, 11 pages.
(Continued)

*Primary Examiner* — Peter S Vasat
*Assistant Examiner* — Ned T Heffner
(74) *Attorney, Agent, or Firm* — McDermott Will & Emery LLP

(57) ABSTRACT

A method for controlling mechanical lung ventilation is described. The method may include intermittently switching the airway pressure of the patient from a substantially constant high baseline pressure level to a substantially constant low baseline pressure and vice-versa such that the patient is able to breathe spontaneously in both high and low baseline pressure levels; detecting an inspiration effort by the patient inside a trigger time window that immediately precedes a switching event of the intermittently switching the airway pressure; maintaining a baseline pressure at the level in which the inspiration effort was detected so that the patient can complete the inspiration-exhalation cycle; and switching the baseline pressure level after a delay time.

20 Claims, 6 Drawing Sheets

(51) Int. Cl.
*A61M 16/20* (2006.01)
*A61M 16/08* (2006.01)

(52) U.S. Cl.
CPC . *A61M 16/0833* (2014.02); *A61M 2016/0027* (2013.01); *A61M 2016/0039* (2013.01); *A61M 2205/3553* (2013.01); *A61M 2205/3561* (2013.01); *A61M 2205/3584* (2013.01); *A61M 2205/3592* (2013.01); *A61M 2205/50* (2013.01)

(58) Field of Classification Search
CPC .......................... A61M 16/06–16/0061; A61M 2016/00165–2016/0042; A61M 2230/00; A61M 2230/005; A61M 2230/40–2230/46; A61B 5/00; A61B 5/082–5/097
USPC ........................................ 128/205.27, 205.28
See application file for complete search history.

(56) References Cited

U.S. PATENT DOCUMENTS

| | | | |
|---|---|---|---|
| 5,474,062 A * | 12/1995 | DeVires | A61M 16/00 128/204.18 |
| 5,582,163 A | 12/1996 | Bonassa | |
| 5,909,731 A | 6/1999 | O'Mahony et al. | |
| 6,369,114 B1 | 4/2002 | Weil et al. | |
| 7,246,618 B2 | 7/2007 | Habashi | |
| 7,810,497 B2 | 10/2010 | Pittman et al. | |
| 8,186,344 B2 | 5/2012 | Bonassa | |
| 8,408,203 B2 | 4/2013 | Tham et al. | |
| 8,677,999 B2 | 3/2014 | Allum et al. | |
| 8,876,728 B2 | 11/2014 | Baloa Welzien et al. | |
| 2002/0043264 A1 | 4/2002 | Wickham | |
| 2005/0109340 A1* | 5/2005 | Tehrani | A61M 16/00 128/204.21 |
| 2006/0011195 A1 | 1/2006 | Zarychta | |
| 2007/0000494 A1 | 1/2007 | Banner et al. | |
| 2007/0199566 A1 | 8/2007 | Be'eri | |
| 2008/0072902 A1 | 3/2008 | Setzer et al. | |
| 2008/0295839 A1 | 12/2008 | Habashi | |
| 2008/0295840 A1 | 12/2008 | Glaw | |
| 2010/0218766 A1 | 9/2010 | Milne | |
| 2011/0232644 A1 | 9/2011 | Doyle | |
| 2012/0024286 A1 | 2/2012 | Boring | |
| 2012/0179061 A1 | 7/2012 | Ramanan et al. | |
| 2012/0216811 A1 | 8/2012 | Kimm et al. | |
| 2013/0074844 A1 | 3/2013 | Kimm et al. | |
| 2013/0125883 A1 | 5/2013 | Bonassa et al. | |
| 2015/0290407 A1 | 10/2015 | Bonassa | |
| 2015/0290409 A1 | 10/2015 | Bonassa | |

FOREIGN PATENT DOCUMENTS

| | | |
|---|---|---|
| WO | WO-2012085748 A1 | 6/2012 |
| WO | WO-2013175394 A1 | 11/2013 |

OTHER PUBLICATIONS

International Search Report and Written Opinion for Application No. PCT/US2015/021590, dated May 29, 2015, 15 pages.
International Search Report and Written Opinion for Application No. PCT/US2015/021591, dated Jul. 1, 2015, 13 pages.
Borrello et al, "Modeling and Control of Systems for Critical Care Ventilation", 2005, pp. 2166-2180.
Chen et al., "Comparisons between Circle and Structural Models in Lung Ventilation Reconstruction by Electrical Impedance Tomography", 2008 IEEE, pp. 53-57.
Favre et al., "Closed-Loop Control of a Continuous Positive Airway Pressure Device", 2003 IEEE, pp. 419-422.
Harris et at., "Continuous Monitoring of Lung Ventilation With Electrical Impedance Tomography", 1992 IEEE, pp. 1754-1755.
Laubscher et al., "An adaptive lung ventilation controller," 1994 IEEE, pp. 51-59.

* cited by examiner

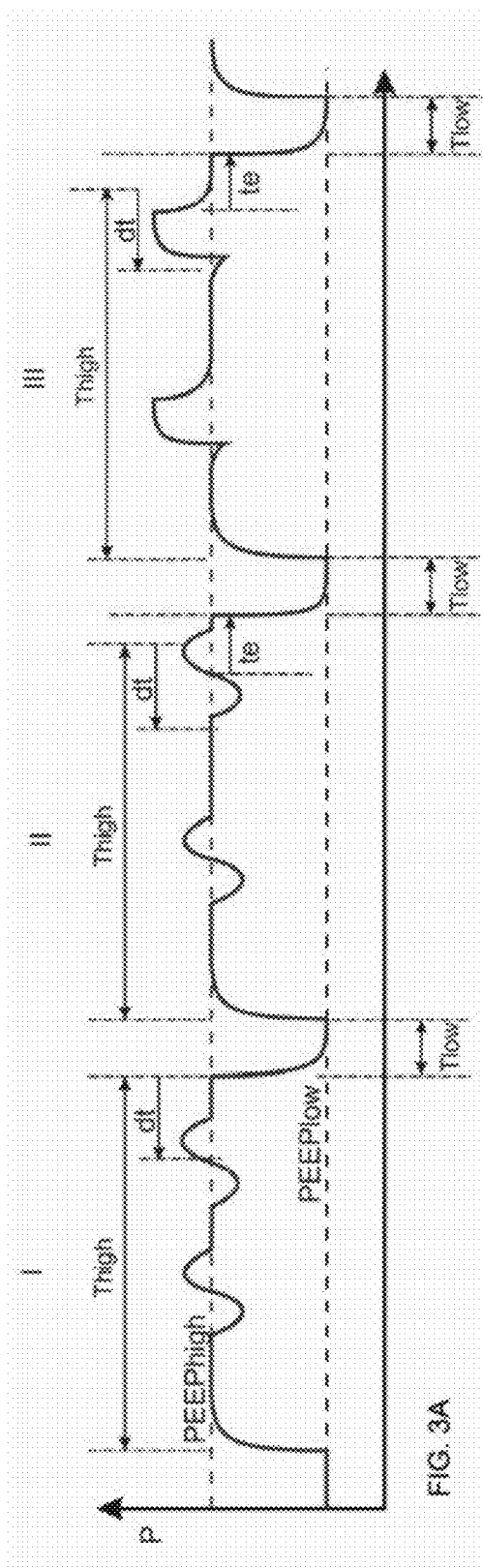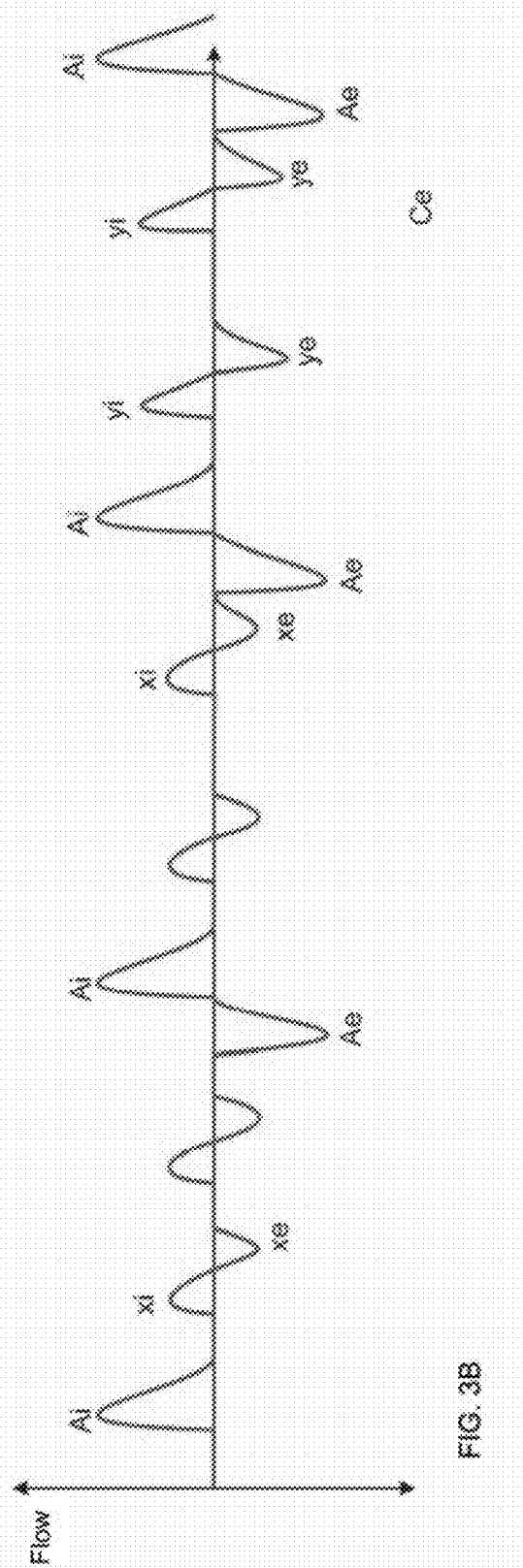
FIG. 3A
FIG. 3B

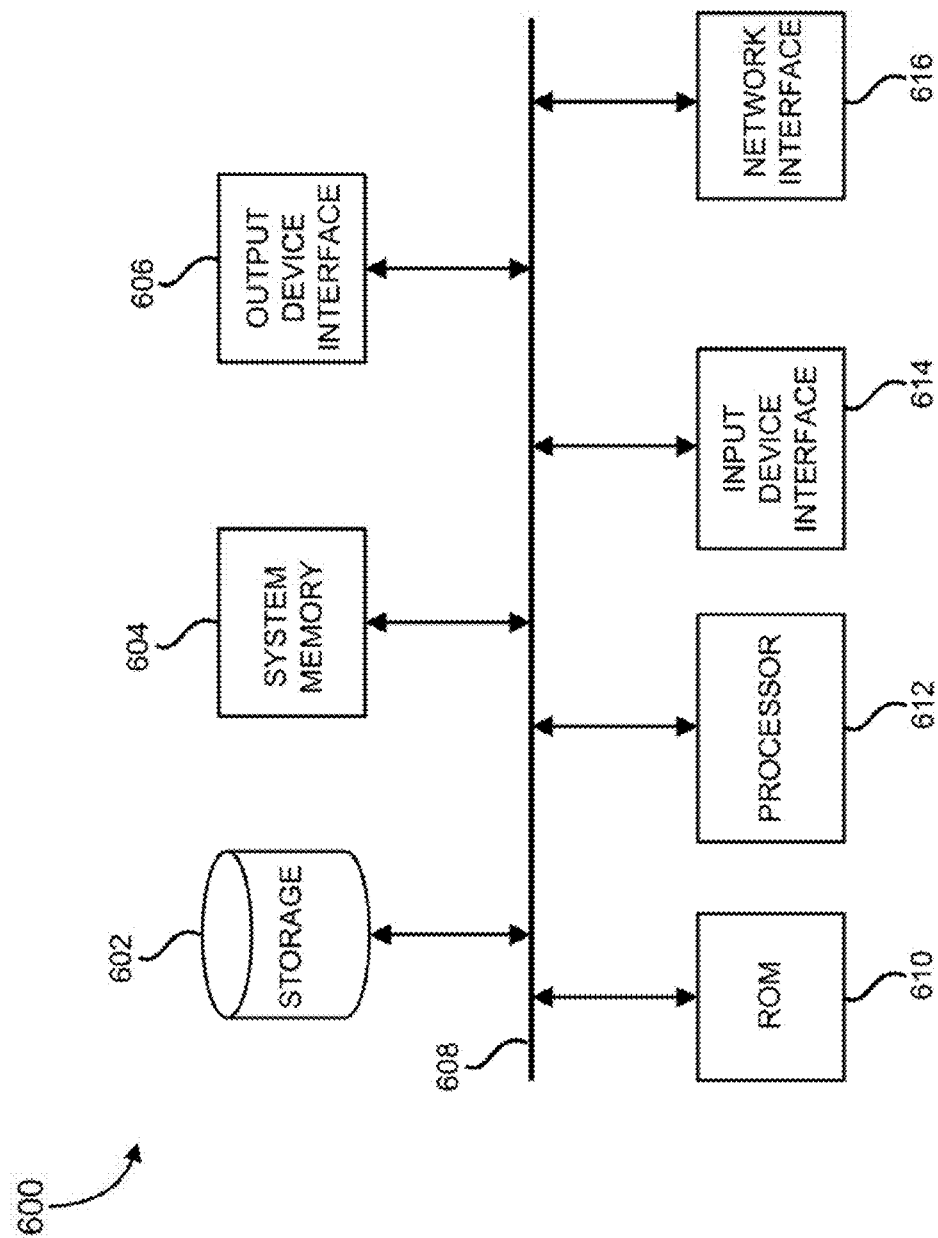

METHODS FOR CONTROLLING MECHANICAL LUNG VENTILATION

TECHNICAL FIELD

The present disclosure generally relates to providing lung ventilation assistance to patients requiring respiratory support, and more particularly to a method for controlling airway pressure release ventilation to deliver respiratory cycles to a patient, providing $CO_2$ removal from volumes above and below the functional residual capacity (FRC) in a synchronized mode.

BACKGROUND

A patient requiring lung ventilation support is usually connected to a mechanical ventilator that applies a positive pressure to insufflate a volume mixture of air and oxygen to the lungs. The positive inspiratory pressure (PIP) cycles are typically applied intermittently and patient exhales to a baseline pressure, also known as Positive End Expiratory Pressure (PEEP), which is usually higher than the atmospheric pressure. In a patient with impaired lung mechanics, the peak pressure obtained by the sum of inspiratory (PIP) and expiratory (PEEP) pressures may result in elevated pressures that can be harmful for the patient's respiratory system.

SUMMARY

Aspects of the subject technology relate to a method capable of enhancing an Airway Pressure Release Ventilation (APRV) mode. In accordance with certain aspects, a method is provided for controlling artificial lung ventilation in a patient wherein the positive pressure cycles (e.g., mandatory or spontaneous) are synchronized with the switch/change of PEEP between two pressure levels in a way to avoid overlapping, improving patient comfort and providing ventilation above and below baseline FRC.

In accordance with certain aspects, a method is provided for controlling artificial lung ventilation in a patient. The method may allow monitoring ventilation data/information/curves in a clear and easy way by an operator, so that the operator can correctly adjust the ventilator parameters, improving patient comfort.

In accordance with certain aspects, a method is provided for controlling artificial lung ventilation in a patient that minimizes or at least reduces the risks related to undesired increasing of expiratory flow and volume, gas trapping and $CO_2$ rebreathing.

In accordance with certain aspects, a method is provided for controlling artificial lung ventilation in a patient, capable of increasing ventilation efficiency and minimizing or at least reducing the risks of lung stress damage.

In accordance with certain aspects, a method is provided for delivering respiratory cycles for patients requiring lung ventilation support, capable of intercalating: (i) positive pressure cycles over a baseline pressure, promoting $CO_2$ removal above Functional Residual Capacity—FRC; and (ii) negative pressure cycles in relation to the baseline pressure to remove $CO_2$ from the FRC, allowing monitoring of both tidal volumes above FRC and tidal volume of FRC.

Various aspects of the subject technology may be achieved by a method for controlling mechanical lung ventilation, comprising: (i) supplying a breathing gas to the airway of a patient; (ii) intermittently switching the airway pressure of the patient from a substantially constant high baseline pressure level to a substantially constant low baseline pressure and vice-versa, the patient being able to breathe spontaneously in both high and low baseline pressure levels; (iii) detecting an inspiration effort by the patient inside a trigger time window that immediately precedes the switching event of the previous step; (iv) allowing the patient to complete the inspiration-exhalation cycle while maintaining the baseline pressure at the level in which the inspiration effort was detected in the previous step; and (v) switching the baseline pressure level after a delay time.

In certain embodiments, both the delay time and the trigger time window may be preset.

In certain embodiments, the method may further comprise: measuring expiratory flow from the beginning of exhalation inside the trigger time window; comparing the measured expiratory flow to a preset level of flow trigger; and switching the baseline pressure level after the delay time if the measured expired flow is equal or less than the preset level of flow trigger. In some implementations, the delay time is set to allow a preset percentage of expiratory flow in relation to the preset level of flow trigger.

In certain embodiments, the method can be applied to spontaneous breathing cycles, in a transition of baseline pressure level from a high level to a low level. In such embodiments, the method may comprise (e.g., inside the preset trigger time window at a substantially constant high baseline pressure level): opening a flow valve of a ventilator to sustain inspiration of the patient; and simultaneously keeping an exhalation valve of the ventilator closed to maintain baseline pressure level at the substantially constant high baseline pressure level. In such embodiments, the method may further comprise: controlling the opening of the exhalation valve to allow complete exhalation at the high baseline pressure level; and opening the exhalation valve after the delay time to release the baseline pressure level from the substantially constant high baseline pressure level to the substantially constant low baseline pressure level.

In certain embodiments, the method can be applied to spontaneous breathing cycles, in a transition of baseline pressure level from a low level to a high level. In such embodiments, the method may comprise (e.g., inside the preset trigger time window at a substantially constant low baseline pressure level): opening a flow valve of a ventilator to sustain inspiration of the patient; and simultaneously keeping an exhalation valve of the ventilator closed to maintain baseline pressure level at the substantially constant low baseline pressure level. In such embodiments, the method may further comprise: controlling the opening of the exhalation valve at the substantially constant low baseline pressure; opening the flow valve after a preset delay time to restore baseline pressure level from the substantially constant low baseline pressure to the substantially constant high baseline pressure.

In certain embodiments, the method may further comprise supplying a support pressure to the patient in a spontaneous breathing cycle, the support pressure being set in a Pressure Support Ventilation (PSV) mode of a ventilator.

In certain embodiments, the method can be applied to Pressure Supported Ventilation cycles, in a transition of baseline pressure level from a high level to a low level. In such embodiments, the method comprises the steps of (e.g., inside the preset trigger time window at a substantially constant high baseline pressure level): opening a flow valve of the ventilator to increase pressure to a set value of the support pressure, said value being above the high baseline pressure; and simultaneously keeping the exhalation valve of the ventilator closed. In this embodiment, the method further comprises the steps of controlling the opening of the exhalation valve at the substantially constant high baseline pressure; and opening the exhalation valve after a preset delay time to release baseline pressure level from the substantially constant high baseline pressure to the substantially constant low baseline pressure.

In certain embodiments, the method can be applied to Pressure Supported Ventilation cycles, in a transition of baseline pressure level from a low level to a high level. In such embodiments, the method may comprise (e.g., inside the preset trigger time window at a substantially constant low baseline pressure level): opening a flow valve of the ventilator to increase pressure to a value set of the support pressure, the value being above the low baseline pressure; and simultaneously keeping the exhalation valve of the ventilator closed. In such embodiments, the method may further comprise: controlling the opening of the exhalation valve at the substantially constant low baseline pressure; and opening the flow valve after a preset delay time to restore baseline pressure level from the substantially constant low baseline pressure to the substantially constant high baseline pressure.

The subject technology is illustrated, for example, according to various aspects described below. Various examples of aspects of the subject technology are described as numbered clauses or embodiments (1, 2, 3, etc.) for convenience. These are provided as examples and do not limit the subject technology. It is noted that any of the dependent clauses may be combined in any combination with each other or one or more other independent clauses, to form an independent clause. The following is a non-limiting summary of some embodiments presented herein:

Clause 1. A method for controlling mechanical lung ventilation, the method comprising: supplying a breathing gas to the airway of a patient; intermittently switching the airway pressure of the patient from a substantially constant high baseline pressure level to a substantially constant low baseline pressure and vice-versa such that the patient is able to breathe spontaneously in both high and low baseline pressure levels; detecting an inspiration effort by the patient inside a trigger time window that immediately precedes a switching event of the intermittently switching the airway pressure; maintaining a baseline pressure at the level in which the inspiration effort was detected so that the patient can complete the inspiration-exhalation cycle; and switching the baseline pressure level after a delay time.

Clause 2. The method of clause 1 or any of the other clauses, wherein the delay time is preset.

Clause 3. The method of clause 1 or any of the other clauses, further comprising: measuring expiratory flow from a beginning of exhalation inside the trigger time window; comparing the measured expiratory flow to a preset level of flow trigger; and switching a baseline pressure level after the delay time when the measured expired flow is equal or less than the preset level of flow trigger.

Clause 4. The method of clause 3 or any of the other clauses, wherein the delay time is set to allow a preset percentage of expiratory flow in relation to the preset level of flow trigger.

Clause 5. The method of clause 1 or any of the other clauses, wherein the trigger time window is preset.

Clause 6. The method of clause 1 or any of the other clauses, further comprising: opening, inside the preset trigger time window at a substantially constant high baseline pressure level, a flow valve of a ventilator to sustain inspiration of the patient; and simultaneously keeping an exhalation valve of the ventilator closed to maintain baseline pressure level at the substantially constant high baseline pressure level.

Clause 7. The method of clause 6 or any of the other clauses, further comprising: controlling the opening of the exhalation valve to allow complete exhalation at the high baseline pressure level; and opening the exhalation valve after the delay time to release the baseline pressure level from the substantially constant high baseline pressure level to the substantially constant low baseline pressure level.

Clause 8. The method of clause 1, further comprising: opening, inside the preset trigger time window at a substantially constant low baseline pressure level, a flow valve of a ventilator to sustain inspiration of the patient; and simultaneously keeping an exhalation valve of the ventilator closed to maintain baseline pressure level at the substantially constant low baseline pressure level.

Clause 9. The method of clause 8 or any of the other clauses, further comprising: controlling the opening of the exhalation valve at the substantially constant low baseline pressure; and opening the flow valve after a preset delay time to restore baseline pressure level from the substantially constant low baseline pressure to the substantially constant high baseline pressure.

Clause 10. The method of clause 1 or any of the other clauses, further comprising supplying a support pressure to the patient in a spontaneous breathing cycle, the support pressure being set in a Pressure Support Ventilation mode of a ventilator.

Clause 11. The method of clause 10 or any of the other clauses, further comprising: opening, inside the preset trigger time window at a substantially constant high baseline pressure level, a flow valve of the ventilator to increase pressure to a set value of the support pressure, said value being above the high baseline pressure, and simultaneously keeping the exhalation valve of the ventilator closed.

Clause 12. The method of clause 11 or any of the other clauses, further comprising: controlling the opening of the exhalation valve at the substantially constant high baseline pressure; and opening the exhalation valve after a preset delay time to release baseline pressure level from the substantially constant high baseline pressure to the substantially constant low baseline pressure.

Clause 13. The method of clause 10 or any of the other clauses, further comprising: opening, inside the preset trigger time window at a substantially constant low baseline pressure level, a flow valve of the ventilator to increase pressure to a value set of the support pressure, said value being above the low baseline pressure; and simultaneously keeping the exhalation valve of the ventilator closed.

Clause 14. The method of clause 13 or any of the other clauses, further comprising: controlling the opening of the exhalation valve at the substantially constant low baseline pressure; and opening the flow valve after a preset delay time to restore baseline pressure level from the substantially constant low baseline pressure to the substantially constant high baseline pressure.

Clause 15. A system for controlling mechanical lung ventilation, the system comprising: one or more processors; and a memory including instructions that, when executed by the one or more processors, cause the one or more processors to: supply a breathing gas to the airway of a patient; intermittently switch the airway pressure of the patient from a substantially constant high baseline pressure level to a substantially constant low baseline pressure and vice-versa such that the patient is able to breathe spontaneously in both high and low baseline pressure levels; detect an inspiration effort by the patient inside a trigger time window that immediately precedes a switching event of the intermittently switched the airway pressure; maintain a baseline pressure at the level in which the inspiration effort was detected so that the patient can complete the inspiration-exhalation cycle; and switch the baseline pressure level after a delay time.

Clause 16. A machine-readable medium comprising instructions stored therein, which when executed by a machine, cause the machine to perform operations, the machine-readable medium comprising: instructions for supplying a breathing gas to the airway of a patient; instructions for intermittently switching the airway pressure of the patient from a substantially constant high baseline pressure level to a substantially constant low baseline pressure and vice-versa such that the patient is able to breathe spontaneously in both high and low baseline pressure levels; instructions for detecting an inspiration effort by the patient inside a trigger time window that immediately precedes a switching event of the intermittently switching the airway pressure; instructions for maintaining a baseline pressure at the level in which the inspiration effort was detected so that the patient can complete the inspiration-exhalation cycle; and instructions for switching the baseline pressure level after a delay time.

Clause 17. The machine-readable medium of clause 16 or any of the other clauses, further comprising: instructions for measuring expiratory flow from a beginning of exhalation inside the trigger time window; instructions for comparing the measured expiratory flow to a preset level of flow trigger, and instructions for switching a baseline pressure level after the delay time when the measured expired flow is equal or less than the preset level of flow trigger.

Clause 18. The machine-readable medium of clause 16 or any of the other clauses, further comprising: instructions for opening, inside the preset trigger time window at a substantially constant high baseline pressure level, a flow valve of a ventilator to sustain inspiration of the patient; and instructions for simultaneously keeping an exhalation valve of the ventilator closed to maintain baseline pressure level at the substantially constant high baseline pressure level.

Clause 19. The machine-readable medium of clause 16 or any of the other clauses, further comprising: instructions for opening, inside the preset trigger time window at a substantially constant low baseline pressure level, a flow valve of a ventilator to sustain inspiration of the patient; and instructions for simultaneously keeping an exhalation valve of the ventilator closed to maintain baseline pressure level at the substantially constant low baseline pressure level.

Clause 20. The machine-readable medium of clause 16 or any of the other clauses, further comprising instructions for supplying a support pressure to the patient in a spontaneous breathing cycle, the support pressure being set in a Pressure Support Ventilation mode of a ventilator.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 3A is graphical representation of airway pressure for APRV according to a second example method.

FIG. 3B is a graphical representation of an associated flow curve corresponding to the pressure curve shown in FIG. 3A for APRV according to the second example method.

FIG. 6 conceptually illustrates an electronic system with which some aspects of the subject technology can be implemented.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Initially, a first example ventilator and first example method will be described to compare and contrast other aspects of the present disclosure. A first example ventilator may offer APRV mode with the possibility to change (switch) from two PEEP levels: PEEPlow and PEEPhigh, also with the alternative of augmenting spontaneous breathing cycles with Pressure Support Ventilation (PSV) to reduce patient's work of breathing. As a result, there may be two types of cycle in the same mode: above and below established FRC.

However, the two distinct cycle types can occur simultaneously: (i) an inspiratory spontaneous pressure supported cycle may terminate earlier, at the beginning of a release period wherein PEEPhigh is reduced to PEEPlow, also reducing the volume ventilated in this cycle; or (ii) the restoration of PEEPhigh occurs with an inspiratory effort, replacing a PSV cycle by a PEEPlow to PEEPhigh gradient, which may result in losing one positive pressure spontaneous cycle or losing one FRC volume.

In an attempt to reduce this cycle conflict, some configurations of the first example ventilator may be able to synchronize the release of PEEPhigh with the beginning of expiratory phase of a spontaneous cycle, and also the restoration of PEEPhigh with an inspiratory effort. Nevertheless, these features per se may not be capable of avoiding the overlapping of spontaneous ventilation and FRC ventilation.

Figures 2A, 2B:
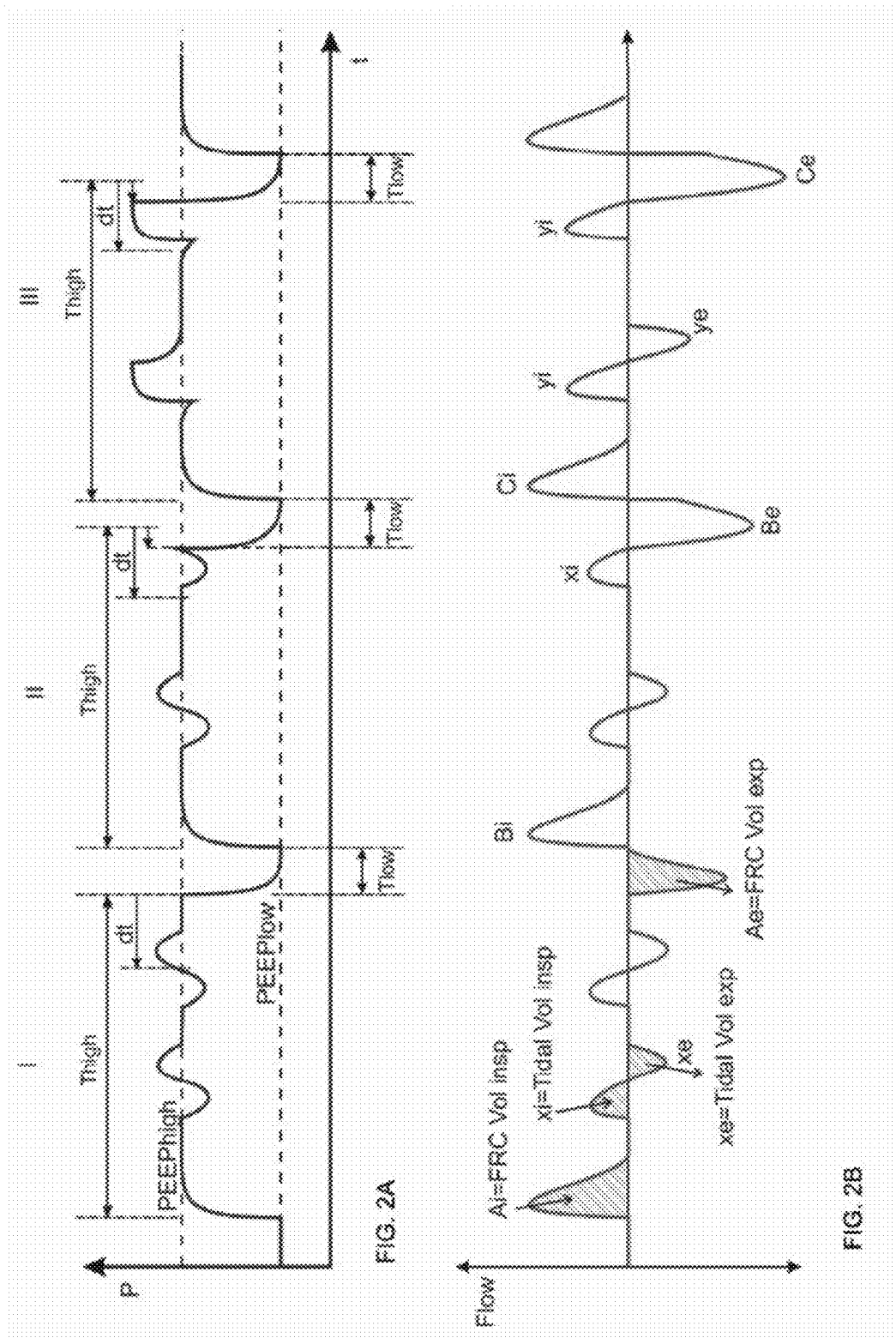
FIG. 2A is a graphical representation of airway pressure for APRV according to a first example method.
FIG. 2B is a graphical representation of an associated flow curve corresponding to the pressure curve shown in FIG. 2A for APRV according to the first example method.

FIG. 2A illustrates an example of characteristic pressure curves of APRV, where it can be noted that baseline pressure remains at PEEPhigh level during a period of Thigh and switches to PEEPlow level during a period of Tlow, Tlow being short compared to Thigh and representing a brief release of time from a higher to a lower baseline pressure level. This release period may allow the exhale of the FRC volume from the baseline pressure corresponding to the PEEPhigh level to the baseline pressure corresponding to the PEEPlow level. As baseline pressure returns to PEEPhigh, a fresh FRC volume may be inspired.

FIG. 2B illustrates an example of flow curves corresponding to pressure curves. In the example of FIG. 2B, the areas Ai, Bi and Ci represent fresh inspired FRC volumes that occur during the switch from PEEPlow to PEEPhigh. The areas Ae, Be and Ce represent released FRC volumes during Tlow.

More specifically, the example of FIGS. 2A-2B shows three particular situations: portions I, II and III of the curves. Portion I illustrates a situation where the patient is breathing spontaneously at PEEPhigh; in this level, an inspiratory effort causes a drop in the pressure and volume inhalation, represented by area xi in flow curve. When the patient exhales a volume xe, the pressure increases again. In portion I, the Tidal Volumes (xi and xe) and also the FRC volume (Ai and Ae) can be distinguished because patient effort takes place far from the baseline pressure switch, for example.

In portion II of the example of FIGS. 2A-2B, a situation where the patient effort takes place closer to the end of Thigh is illustrated. In this situation, in general, the first example ventilator measures a trigger window period dt from the end of Thigh, and any effort that takes place in this window period dt may) trigger the release time at the beginning of exhalation of this inspiratory cycle. Comparing to previous situation I, it can be noted that during the release time, both Tidal Volume xe and FRC volume Ae will typically have to be exhaled at the same time, resulting in a total released volume of Be(=xe+Ae). However, in this case, the release time may be not enough to allow complete exhalation and therefore part of the exhaled gas will likely be trapped and will return to FRC volume CI. Also, the sum of Tidal and FRC volumes may exceed the low volume (e.g., 6 ml/kg) adequate for a protective ventilation strategy.

The last portion III of the example of FIGS. 2A-2B shows an exacerbation of the situation described in portion II. In portion III, a pressure support may be used to augment spontaneous tidal volume yi, in order to decrease patient effort, reducing work of breathing and preventing muscular fatigue. Again, a patient effort that takes place near the end of Thigh may trigger pressure release at the beginning of the exhalation in the pressure supported cycle, resulting in larger volume Ce to release, formed by tidal volume ye and FRC volume Ae.

This first example method of APRV control may result in overlapping of FRC and tidal volumes, which may cause a volume increase to a value that exceeds the safe range and also may cause an air trapping that reduces $CO_2$ washout efficiency.

Another approach similar to the first example method of APRV is BiPAP or Bi-level Ventilation, the difference being that the release periods in BiPAP are usually longer than in APRV, thereby allowing the patient to breath spontaneously in both high and low baseline pressure levels.

For example, high expiratory pressures (PEEP) and low inspiratory volumes/pressures may be used in patients with acute respiratory distress to provide protective ventilation, minimizing the risk of iatrogenic lung injury. In this situation, the use of low inspiratory volumes may be recommended in order to reduce the risks of volutrauma. On the other hand, this strategy is generally unable to promote adequate $CO_2$ washout, conducting to a hypercapnia situation. In view of this, APRV may be an alternative to improve $CO_2$ removal during protective ventilation.

Figure 4A:
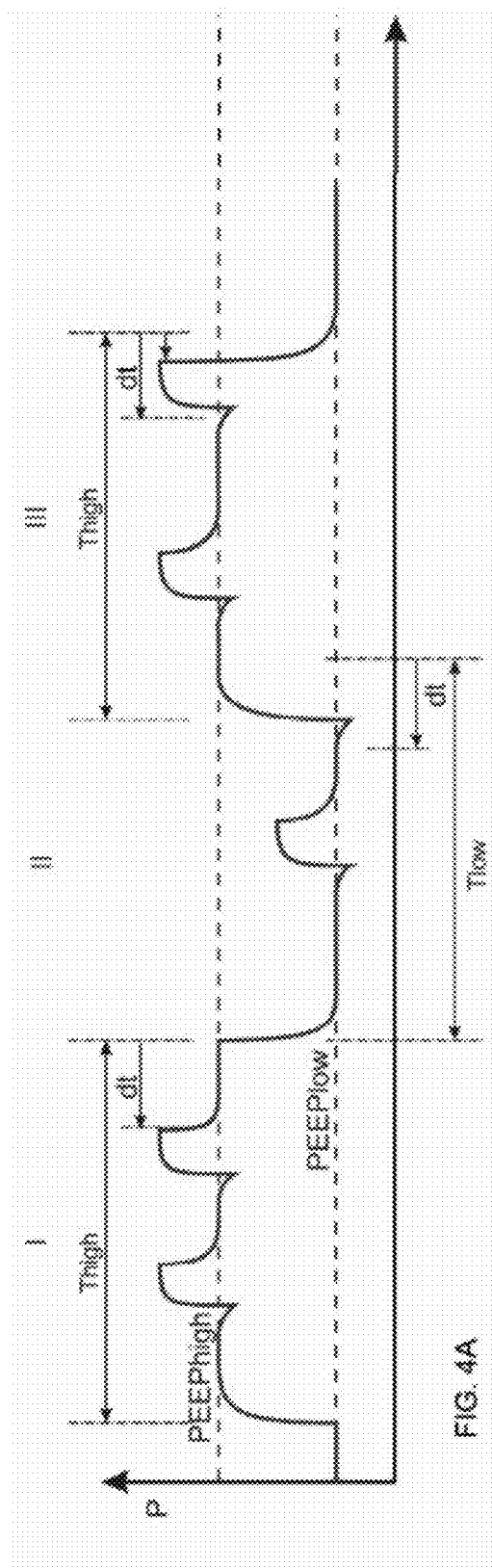
FIG. 4A is a graphical representation of airway pressure for Bi-level Ventilation according to the first example method.
Figure 4B:
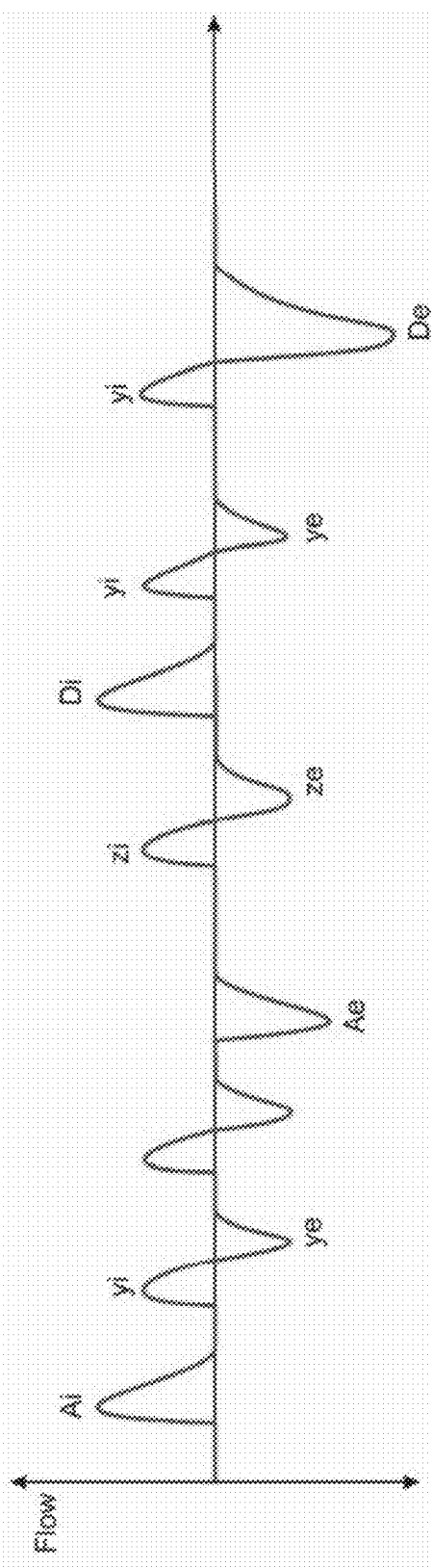
FIG. 4B is a graphical representation of an associated flow curve corresponding to the pressure curve shown in FIG. 4A for Bi-level Ventilation according to the first example method.

A first example BiPAP or Bi-level Ventilation is illustrated in FIGS. 4A-4B. FIGS. 4A-4B shows examples of the patient breaths at PEEPhigh and PEEPlow in Thigh and Tlow, respectively. In this case, the spontaneous cycles may be assisted by Pressure Support, however, similar characteristics would likely be also observed for non-assisted cycles. As can be seen in portion I of the curves, patient efforts and cycles may occur far from the transition point and, as previously discussed, there may be no overlapping between tidal and FRC volumes.

In portion II of the example of FIGS. 4A-4B, the patient also can breathe at PEEPlow in the Tlow period until transition for next Thigh. Nevertheless, if patient's effort takes place near the end of Tlow period, which may be defined by a trigger window dt from the end of Tlow, this effort may trigger the end of the release time, changing baseline pressure to PEEPhigh and starting Thigh. Thus, patient inspiration effort may coincide with PEEPhigh restoration, and the tidal volume may be supplied by FRC volume. As patient starts breathing at PEEPlow and finishes at PEEPhigh, the exhalation is almost completely aborted in this cycle, which may be undesired in certain instances. Comparing to portion I, where the baseline pressure transition takes place independently from the patient effort, the volumes of FRC Ai (inspired) and Ae (exhaled), and also tidal volumes yi (inspired) and ye (exhaled) can be identified. When cycle overlapping occurs, inspired volume Di during baseline restoration may take place of a tidal volume zi, without allowing ze to be exhaled, for example. In other words, a spontaneous ventilation cycle was aborted and replaced by baseline pressure transition in the example of FIGS. 4A-4B. This may result in patient discomfort and also may increase muscle load to exhale. In addition, overlapping cycles may abort spontaneous cycles, thereby decreasing minute ventilation in certain situations.

Portion III of FIGS. 4A-4B is the same as Portion III of FIGS. 2A-2B, which was already explained above, and again the overlapping of exhaled spontaneous cycle and FRC volume release in volume De can be identified. This volume De may be larger than volume Ae from nonoverlapped cycles, and may exceed the safe values related to protective ventilation protocol, in certain instances.

Figure 1:
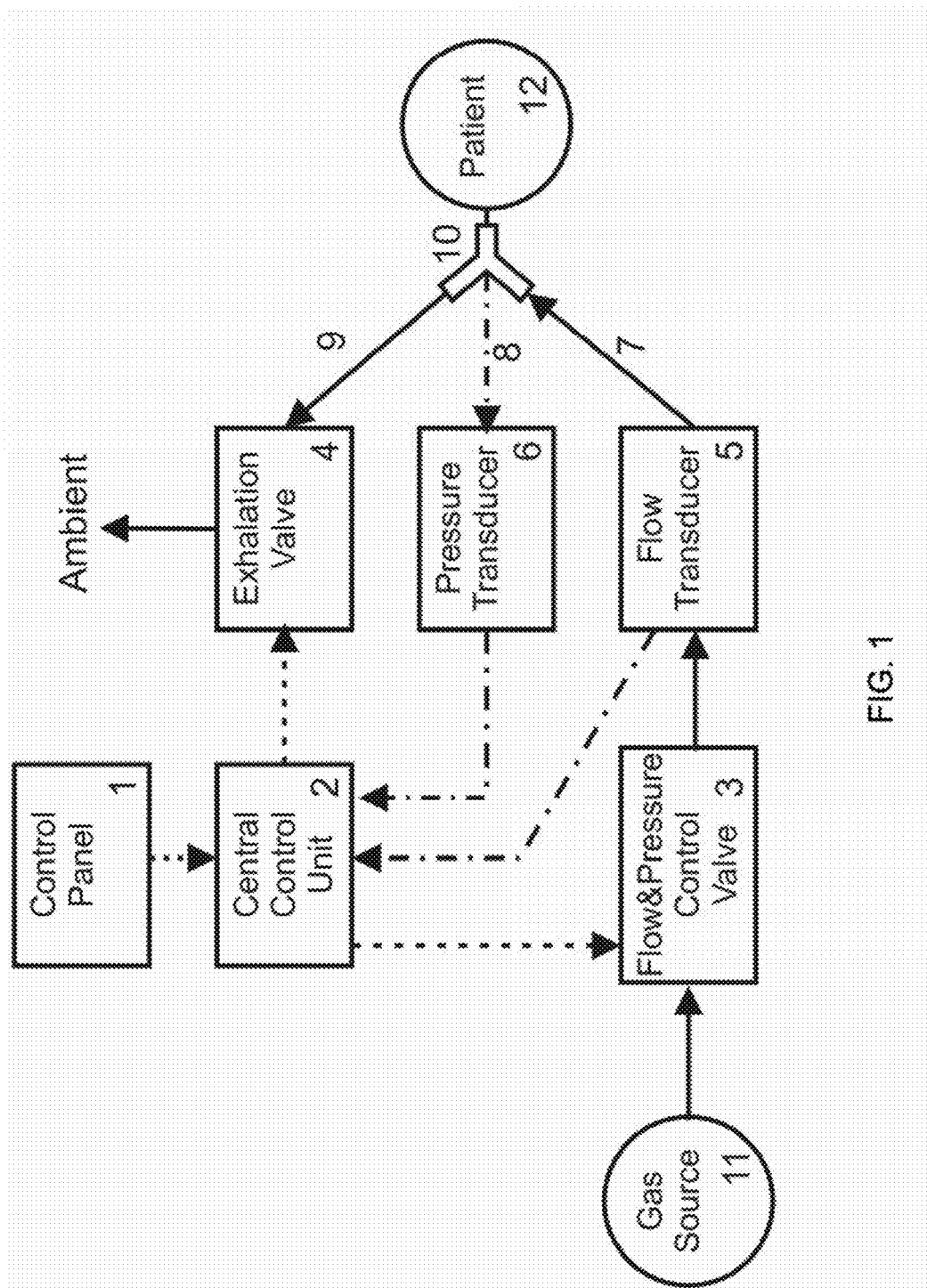
FIG. 1 is a schematic representation of an example of a lung ventilator connected to a patient, in accordance with aspects of the present disclosure.

In view of the first example of FIGS. 2A-2B and 4A-4B, an example ventilator of FIG. 1 and a second example of FIGS. 3A-3B and 5A-5B associated with a second example method and other example methods and aspects of the present disclosure will be descried.

FIG. 1 schematically illustrates an example ventilator system comprising a flow and pressure control valve 3 coupled to a source of gas 11. In certain embodiments, control valve 3 is capable of controlling the inspiratory flow by means of an inspiratory tube 7 coupled to a patient 12 by means of a "Y" type connector 10. The gas from the patient 12 may be exhaled through an exhalation tube 9 coupled to the other end of the "Y" connector 10. The exhaled gas may be controlled by an exhalation valve 4. The pressure in the airway of the patient 12 is sent from the "Y" connector 10, which is coupled to a pressure transducer 6 by means of a tube 8, for example.

In certain embodiments, the inspiratory flow may be measured by the flow transducer 5 positioned downstream from the flow and pressure control valve 3. Both inspiratory flow and airway pressure signals coming from flow transducer 5 and pressure transducer 6, respectively, together with parameters adjusted in the control panel 1, may be used by the central control unit 2 to control flow and pressure control valve 3 and exhalation valve 4.

In certain embodiments, flow and pressure 3 and exhalation 4 control valves are servo controlled by a microprocessor, but one or more of these valves may be activated by solenoids and/or pneumatics, for example.

The example ventilator system is capable of executing of methods of the present disclosure. However, the system is not limited to any particular arrangement and therefore, aspects of the system can be embodied in various alternatives. For example, the flow and pressure valve function may be performed by a compressor or turbine, in accordance with some embodiments. In other embodiments, the respiratory circuit may only comprise a single inspiratory branch and the function of the exhalation valve may be performed by a single orifice at the patient's connection. The inspiratory and/or pressure flow can be measured in different positions or even measured or estimated by different means, in accordance with some embodiments.

It is to be appreciated that aspects of the subject technology can be implemented in both ventilation systems intended for invasive ventilation and non-invasive ventilation, considering adjustments that may be required to compensate the volume of gas which is lost (e.g., in interfaces).

In certain embodiments, the example ventilator system may use a control unit that receives flow and pressure signals coming from respective transducers to control exhalation, flow and pressure values. From a control panel, the parameters values may be adjusted to control respiratory cycles. In certain configurations, the one or more of following control parameters may be required depending on the desired ventilator strategy. In some implementations, for example, to control respiratory cycles (controlled, assisted or spontaneous), one or more of the following control parameters may be required: Respiratory Frequency FR; Sensitivity S; Inspiratory Time TI; Controlled Pressure PC; and Support Pressure PS. In other implementations, for example, to control baseline, one or more of the following control parameters may be required: pressure (PEEP): PEEPhigh; Thigh; PEEPlow; and Tlow.

In accordance with aspects of the subject technology, a method may allow monitoring and controlling the mechanical lung ventilation system by providing ventilator support that augments pressure and volume (Tidal Volume) over a baseline pressure. In addition, the method is capable of changing baseline pressure from PEEPhigh to PEEPlow and vice-versa at a predetermined ratio to renew the Residual Volume associated with the Functional Residual Capacity (FRC) implemented with any adaptations, if desired.

FIGS. 3A-3B and 5A-5B show the curves of Airway Pressure Release Ventilation (APRV) and Bi-level Ventilation modes, respectively, according to a second example of the present disclosure. Both modes illustrate the switching of the baseline pressure (PEEP) between two levels. These curves demonstrate at least some differences and associated improvements resulting from the control method of the second example over the first example (as shown in FIGS. 2 and 4).

For example, FIGS. 3A-3B show example pressure and flow curves resulting from an embodiment in accordance with the second example of present disclosure, in similar scenarios of FIGS. 2A-2B (first example).

Portion I of the example of FIGS. 3A-3B shows a situation where the patient 12 is breathing spontaneously at PEEPhigh. In this level, an inspiratory effort causes a drop in the pressure and volume inhalation, represented by area xi in flow curve. When the patient 12 exhales a volume xe, the pressure increases again. The Tidal Volumes (xi and xe) and also the FRC volume (Ai and Ae) can be identified since patient effort takes place far from the baseline pressure switch. Therefore, whenever the patient effort takes place out of a trigger window dt, there is no conflict between tidal volume and FRC volume inspiration and exhalation, in accordance with this example situation.

In portion II of the example of FIGS. 3A-3B, a cycle inside trigger window dt is detected, the flow valve 3 is opened to sustain inspiration while the exhalation valve is kept closed to maintain baseline pressure at PEEPhigh level. Then, the method may allow the execution of one or more of the following operations: measuring the flow and time up to completion of tidal volume xi at the end of inspiration; initiating exhalation of tidal volume xe by controlling the opening of exhalation valve 4 at the same baseline pressure PEEPhigh level; measuring the time from the beginning of exhalation as well as the expired flow; and opening the exhalation valve 4 to release baseline pressure from PEEPhigh to PEEPlow after a preset release delay time te.

For example, this allows exhaling FRC volume Ae, and also allows measuring the period of time from the beginning of the release. When this period of time reaches preset time Tow, the exhalation valve 4 may be closed and the flow valve 3 may be opened to increase baseline pressure to PEEPhigh and restore the volume of FRC Ai. It is also to be noted that, in the certain embodiments, the exhalation of tidal volume xe and FRC volume Ae takes place at different moments, separated by delay time te. In this way, the exhalation of FRC volume Ae takes place dissociated from the exhalation of tidal volume xe, avoiding tidal volume and FRC volume overlapping. Therefore, the undesired increase of expiratory flow and volume, gas trapping and $CO_2$ rebreathing, that can reduce ventilation efficiency and increase lung stress damage, are all minimized or at least reduced by aspects of the present disclosure.

The last portion III of the example of FIGS. 3A-3B illustrates a situation in which pressure support PS is used to augment spontaneous tidal volume yi. In this portion, the method may allow for one or more of the following operations: detecting a cycle inside the trigger window dt; opening the flow valve 3 to increase pressure to a value set in the Pressure Support PS control while keeping exhalation 4 valve closed, this value being above baseline pressure PEEPhigh; measuring the flow and time up to completion of tidal volume yi at end of inspiration; initiating exhalation of tidal volume ye by controlling the opening of exhalation at the same baseline pressure PEEPhigh; measuring the time from the start of exhalation as well as the expired flow; opening the exhalation valve 4 to release baseline pressure from PEEPhigh to PEEPlow after a preset release delay time te, allowing FRC volume exhales Ae; measuring the period of time from the beginning of the release; closing the exhalation valve 4 after the period of the previous step reaches preset value Tlow; and opening the flow valve 3 to increase baseline pressure to PEEPhigh and restore the volume of FRC Ai.

As in portion II of the example of FIG. 3, where the patient breaths spontaneously with no support, the exhalation of tidal volume of the supported spontaneous cycle ye and FRC volume Ae takes place at different times, separated by delay time te.

In certain embodiments of the present disclosure, release delay time te is automatically calculated by measuring expiratory flow from the beginning of exhalation of tidal volume xe; and comparing it to a flow trigger preset level ft. If the actual expired flow is equal or less than trigger preset level ft, the delay time te is terminated and the release is started. The release time delay te can be set to allow a preset percentage of expiratory flow (and consequently volume), which can be advantageous to avoid gas trapping and optimize gas exchange in patients that present changes in respiratory mechanics.

Comparing portions II and III of the example of FIGS. 2A-2B (first example) and the example of FIGS. 3A-3B (second example), it is easy to identify and distinguish the tidal volumes (xi, xe, yi and ye) and also FRC volumes (Ai and Ae) in FIGS. 3A-3B. On the other hand, in FIGS. 2A-2B, the overlapping makes it difficult (if not nearly impossible) to distinguish between both tidal and FRC volumes during release period, compromising the monitoring by the operator, both for graphical and numerical evaluation.

Figures 5A, 5B:
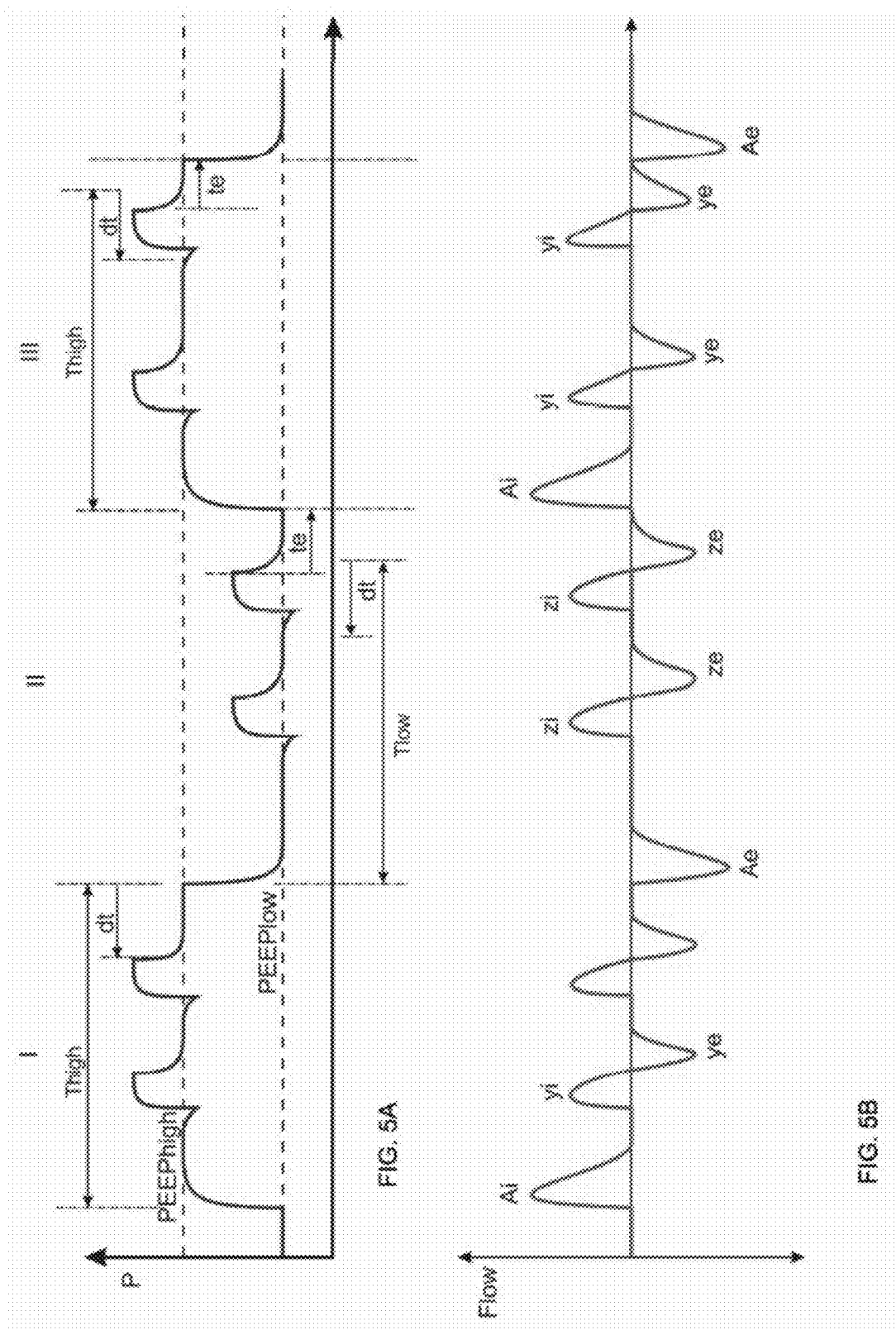
FIG. 5A is graphical representation of airway pressure for Bi-level Ventilation according to the second example method.
FIG. 5B is a graphical representation of an associated flow curve corresponding to the pressure curve shown in FIG. 5A for Bi-level Ventilation according to the second example method.

FIGS. 5A-5B show an example of pressure and flow curves resulting from an example in accordance with certain embodiments of present disclosure, in similar scenarios of the example of FIGS. 4A-4B (first example), when larger Tlow are used, as in BiPAP or Bi-level ventilation.

In portion I of curves in the example of FIGS. 5A-5B, it can be seen that whenever the patient effort is out of a trigger window dt, there is no conflict between tidal volume and FRC volume inspiration and exhalation, as in the example of FIGS. 4A-4B.

In portion II of the curve in the example of FIGS. 5A-5B, during Tlow at PEEPlow, a cycle inside trigger window dt is detected, the flow valve 3 is opened to increase pressure to a value set in the Pressure Support PS control (which is above baseline pressure PEEPlow) while the exhalation valve 4 is kept closed. Then, the method according to the second example of the present disclosure may allow the execution of one or more of the following operations: measuring the flow and time up to completion of tidal volume zi at end of inspiration; initiating exhalation of tidal volume ze by controlling the opening of exhalation valve 4 at the baseline pressure PEEPlow; measuring the time from the beginning of exhalation as well as the expired flow; opening the flow valve 3 to restore baseline pressure from PEEPlow to PEEPhigh after a preset release delay time te, allowing the delivery of FRC volume Ai; and measuring the period of time from the beginning of the delivery of FRC volume Ai to control Thigh period.

Portion III of the example of FIGS. 5A-5B is the same as portion III of the example of FIGS. 3A-3B, and was described and explained above.

As disclosed and illustrated in the examples of FIGS. 3A-3B and 5A-5B, the method may prevent the overlapping of respiratory cycles and baseline pressure releases, thereby improving safety and efficiency. Moreover, aspects of the present disclosure may assure that an inspiratory cycle starts and finishes at the same expiratory pressure, PEEPlow or PEEPhigh, thus improving ventilation above and below Functional Residual Capacity FRC and patient comfort.

The respiratory cycles in the examples described herein are spontaneous cycles unassisted or assisted by Pressure Support, but they may also be of controlled and assisted mandatory cycles type in accordance with other embodiments. Therefore, the aspects of the present disclosure is not limited to spontaneous breathing patients, but can also be applied to other conventional modes of ventilation, where addition of baseline pressure releases may be beneficial. For example, this may be particularly true in protective ventilation protocols, where low volume mandatory cycles are used with elevated baseline PEEP pressures, and where the periodic release of PEEP may improve ventilation without compromising recruitment or exceeding safe volume ranges.

In accordance with various aspects of the subject technology, an example method may be performed for controlling mechanical lung ventilation. The example method may comprise the steps of: supplying a breathing gas to the airway of a patient; intermittently switching the airway pressure of the patient from a substantially constant high baseline pressure level to a substantially constant low baseline pressure and vice-versa, the patient being able to breathe spontaneously in both high and low baseline pressure levels; detecting an inspiration effort by the patient inside a trigger time window that immediately precedes the switching event of the previous step; allowing the patient to complete the inspiration-exhalation cycle while maintaining the baseline pressure at the level in which the inspiration effort was detected in the previous step; and switching the baseline pressure level after a delay time.

In some aspects, the delay time may be preset. The example method may further comprise the steps of: measuring expiratory flow from the beginning of exhalation inside the trigger time window; comparing the measured expiratory flow to a preset level of flow trigger; and switching the baseline pressure level after the delay time if the measured expired flow is equal or less than the preset level of flow trigger.

In some aspects, the delay time may be set to allow a preset percentage of expiratory flow in relation to the preset level of flow trigger. In some aspect, the trigger time window may be preset. The example method may further comprise, inside the preset trigger time window at a substantially constant high baseline pressure level, the steps of: opening a flow valve of a ventilator to sustain inspiration of the patient; and simultaneously keeping an exhalation valve of the ventilator closed to maintain baseline pressure level at the substantially constant high baseline pressure level.

The example method may further comprise the steps of: controlling the opening of the exhalation valve to allow complete exhalation at the high baseline pressure level; and opening the exhalation valve after the delay time to release the baseline pressure level from the substantially constant high baseline pressure level to the substantially constant low baseline pressure level.

The example method may further comprise, inside the preset trigger time window at a substantially constant low baseline pressure level, the steps of: opening a flow valve of a ventilator to sustain inspiration of the patient; and simultaneously keeping an exhalation valve of the ventilator closed to maintain baseline pressure level at the substantially constant low baseline pressure level.

The example method may further comprise the steps of: controlling the opening of the exhalation valve at the substantially constant low baseline pressure; and opening the flow valve after a preset delay time to restore baseline pressure level from the substantially constant low baseline pressure to the substantially constant high baseline pressure.

The example method may further comprise a step of supplying a support pressure to the patient in a spontaneous breathing cycle, the support pressure being set in a Pressure Support Ventilation mode of a ventilator.

The example method may further comprise, inside the preset trigger time window at a substantially constant high baseline pressure level, the steps of: opening a flow valve of the ventilator to increase pressure to a set value of the support pressure, said value being above the high baseline pressure; and simultaneously keeping the exhalation valve of the ventilator closed.

The example method may further comprise the steps of: controlling the opening of the exhalation valve at the substantially constant high baseline pressure; and opening the exhalation valve after a preset delay time to release baseline pressure level from the substantially constant high baseline pressure to the substantially constant low baseline pressure.

The example method may further comprise, inside the preset trigger time window at a substantially constant low baseline pressure level, the steps of: opening a flow valve of the ventilator to increase pressure to a value set of the support pressure, said value being above the low baseline pressure; and simultaneously keeping the exhalation valve of the ventilator closed.

The example method may further comprise the steps of: controlling the opening of the exhalation valve at the substantially constant low baseline pressure; and opening the flow valve after a preset delay time to restore baseline pressure level from the substantially constant low baseline pressure to the substantially constant high baseline pressure.

FIG. 6 conceptually illustrates electronic system 600 with which implementations of the subject technology can be implemented. Electronic system 600, for example, can be, or can include, any of the control panel 1, the central control unit 2, a server, a desktop computer, a laptop computer, a tablet computer, a base station, or generally any electronic device. Such an electronic system includes various types of computer readable media and interfaces for various other types of computer readable media. Electronic system 600) includes bus 608, processing unit(s) 612, system memory 604, read-only memory (ROM) 610, permanent storage device 602, input device interface 614, output device interface 606, and network interface 616, or subsets and variations thereof.

Bus 608 collectively represents system, peripheral, and chipset buses that communicatively connect the numerous internal devices of electronic system 600. In one or more implementations, bus 608 communicatively connects processing unit(s) 612 with ROM 610, system memory 604, and permanent storage device 602. From these various memory units, processing unit(s) 612 retrieves instructions to execute and data to process in order to execute the processes of the subject disclosure. The processing unit(s) can be a single processor or a multi-core processor in different implementations.

ROM 610 stores static data and instructions that are needed by processing unit(s) 612 and other modules of the electronic system. Permanent storage device 602, on the other hand, is a read-and-write memory device. This device is a non-volatile memory unit that stores instructions and data even when electronic system 600 is off. One or more implementations of the subject disclosure use a mass-storage device (such as a magnetic or optical disk and its corresponding disk drive) as permanent storage device 602.

Other implementations use a removable storage device (such as a floppy disk, flash drive, and its corresponding disk drive) as permanent storage device 602. Like permanent storage device 602, system memory 604 is a read-and-write memory device. However, unlike storage device 602, system memory 604 is a volatile read-and-write memory, such as random access memory. System memory 604 stores any of the instructions and data that processing unit(s) 612 needs at runtime. In one or more implementations, the processes of the subject disclosure are stored in system memory 604, permanent storage device 602, and/or ROM 610. From these various memory units, processing unit(s) 612 retrieves instructions to execute and data to process in order to execute the processes of one or more implementations.

Bus 608 also connects to input and output device interfaces 614 and 606. Input device interface 614 enables a user to communicate information and select commands to the electronic system. Input devices used with input device interface 614 include, for example, alphanumeric keyboards and pointing devices (also called "cursor control devices"), touchpads, trackpads, or generally any device capable of receiving user input. Output device interface 606 enables, for example, the display of images generated by electronic system 600. Output devices used with output device interface 606 include, for example, printers and display devices, such as a liquid crystal display (LCD), a light emitting diode (LED) display, an organic light emitting diode (OLED) display, a flexible display, a flat panel display, a solid state display, a projector, or any other device for outputting information. One or more implementations may include devices that function as both input and output devices, such as a touchscreen. In these implementations, feedback provided to the user can be any form of sensory feedback, such as visual feedback, auditory feedback, or tactile feedback; and input from the user can be received in any form, including acoustic, speech, or tactile input.

Finally, as shown in FIG. 6, bus 608 also couples electronic system 600 to a network (not shown) through network interface 616. In this manner, the computer can be a part of a network of computers (such as a local area network ("LAN"), a wide area network ("WAN"), or an Intranet, or a network of networks, such as the Internet. Electronic system 600 may retrieve and/or receive information, e.g. via the network interface 616, from a cloud system, e.g. a cloud storage system. Any or all components of electronic system 600 can be used in conjunction with the subject disclosure.

In one or more implementations, the denominator and numerator of any ratio may be swapped, e.g. the ratio of two areas may be determined by dividing the first area by the second area or the second area by the first area. However, if the denominator and numerator of a ratio are swapped, the value of a threshold that the ratio is compared to may also be swapped accordingly.

Many of the above-described features and applications may be implemented as software processes that are specified as a set of instructions recorded on a computer readable storage medium (alternatively referred to as computer-readable media, machine-readable media, or machine-readable storage media). When these instructions are executed by one or more processing unit(s) (e.g., one or more processors, cores of processors, or other processing units), they cause the processing unit(s) to perform the actions indicated in the instructions. Examples of computer readable media include, but are not limited to, RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, ultra density optical discs, any other optical or magnetic media, and floppy disks. In one or more implementations, the computer readable media does not include carrier waves and electronic signals passing wirelessly or over wired connections, or any other ephemeral signals. For example, the computer readable media may be entirely restricted to tangible, physical objects that store information in a form that is readable by a computer. In one or more implementations, the computer readable media is non-transitory computer readable media, computer readable storage media, or non-transitory computer readable storage media.

In one or more implementations, a computer program product (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

While the above discussion primarily refers to microprocessor or multi-core processors that execute software, one or more implementations are performed by one or more integrated circuits, such as application specific integrated circuits (ASICs) or field programmable gate arrays (FPGAs). In one or more implementations, such integrated circuits execute instructions that are stored on the circuit itself.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that any specific order or hierarchy of blocks in the processes disclosed is an illustration of example approaches. Based upon design preferences, it is understood that the specific order or hierarchy of blocks in the processes may be rearranged, or that all illustrated blocks be performed. Any of the blocks may be performed simultaneously. In one or more implementations, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

As used in this specification and any clauses of this application, the terms "computer", "server", "processor", and "memory" all refer to electronic or other technological devices. These terms exclude people or groups of people. For the purposes of the specification, the terms "display" or "displaying" means displaying on an electronic device.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112 (f) unless the element is expressly recited using the phrase "means for" or, in the case of a method claim, the element is recited using the phrase "step for." Furthermore, to the extent that the term "include." "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. §101, 102, or 103, nor should they be interpreted in such a way.

What is claimed is:

1. A method for controlling mechanical lung ventilation, the method comprising:
   supplying a breathing gas to the airway of a patient;
   controlling a flow control valve and an exhalation valve of a ventilator for intermittently switching the airway pressure of the patient from a substantially constant high baseline pressure level to a substantially constant low baseline pressure and vice-versa such that the patient is able to breathe spontaneously during both a first period of time corresponding to the high baseline pressure level and a second period of time corresponding to the low baseline pressure level;
   detecting an inspiration effort by the patient inside a trigger time window that immediately precedes a switching event of the intermittently switching the airway pressure at the end of the first or second period of time and is substantially shorter than the first period of time;
   controlling the flow control valve and the exhalation valve, responsive to the detecting, for maintaining a baseline pressure at the level in which the inspiration effort was detected by increasing the first period of time or the second period of time by a delay time so that the patient can complete the inspiration-exhalation cycle during the delay time prior to the switching event; and
   controlling the flow control valve and the exhalation valve for switching the baseline pressure level after the delay time.

2. The method of claim 1, wherein the delay time is preset.

3. The method of claim 1, further comprising:
   measuring expiratory flow from a beginning of exhalation inside the trigger time window;
   comparing the measured expiratory flow to a preset level of flow trigger; and
   switching a baseline pressure level after the delay time when the measured expired flow is equal or less than the preset level of flow trigger.

4. The method of claim 3, wherein the delay time is set to allow a preset percentage of expiratory flow in relation to the preset level of flow trigger.

5. The method of claim 1, wherein the trigger time window is preset.

6. The method of claim 5, further comprising:
   opening, inside the preset trigger time window at the substantially constant high baseline pressure level, the flow valve of the ventilator to sustain inspiration of the patient; and
   simultaneously keeping the exhalation valve of the ventilator closed to maintain baseline pressure level at the substantially constant high baseline pressure level.

7. The method of claim 6, further comprising:
   controlling the opening of the exhalation valve to allow complete exhalation at the high baseline pressure level; and
   opening the exhalation valve after the delay time to release the baseline pressure level from the substantially constant high baseline pressure level to the substantially constant low baseline pressure level.

8. The method of claim 5, further comprising:
   opening, inside the preset trigger time window at the substantially constant low baseline pressure level, the flow valve of the ventilator to sustain inspiration of the patient; and
   simultaneously keeping the exhalation valve of the ventilator closed to maintain baseline pressure level at the substantially constant low baseline pressure level.

9. The method of claim 8, further comprising:
   controlling the opening of the exhalation valve at the substantially constant low baseline pressure; and
   opening the flow valve after a preset delay time to restore baseline pressure level from the substantially constant low baseline pressure to the substantially constant high baseline pressure.

10. The method of claim 1, further comprising supplying a support pressure to the patient in a spontaneous breathing cycle, the support pressure being set in a Pressure Support Ventilation mode of the ventilator.

11. The method of claim 10, further comprising:
opening, inside the trigger time window at the substantially constant high baseline pressure level, the flow valve of the ventilator to increase pressure to a set value of the support pressure, said value being above the high baseline pressure; and
simultaneously keeping the exhalation valve of the ventilator closed.

12. The method of claim 11, further comprising:
controlling the opening of the exhalation valve at the substantially constant high baseline pressure; and
opening the exhalation valve after a preset delay time to release the baseline pressure level from the substantially constant high baseline pressure to the substantially constant low baseline pressure.

13. The method of claim 10, further comprising:
opening, inside the trigger time window at the substantially constant low baseline pressure level, a flow valve of the ventilator to increase pressure to a value set of the support pressure, said value being above the low baseline pressure; and
simultaneously keeping the exhalation valve of the ventilator closed.

14. The method of claim 13, further comprising:
controlling the opening of the exhalation valve at the substantially constant low baseline pressure; and
opening the flow valve after a preset delay time to restore baseline pressure level from the substantially constant low baseline pressure to the substantially constant high baseline pressure.

15. A system for controlling mechanical lung ventilation, the system comprising:
one or more processors; and
a memory including instructions that, when executed by the one or more processors, cause the one or more processors to:
supply a breathing gas to the airway of a patient;
intermittently switch the airway pressure of the patient from a substantially constant high baseline pressure level to a substantially constant low baseline pressure and vice-versa such that the patient is able to breathe spontaneously during both a first period of time corresponding to the high baseline pressure level and a second period of time corresponding to the low baseline pressure level;
detect an inspiration effort by the patient inside a trigger time window that immediately precedes a switching event of the intermittently switched the airway pressure at the end of the first period of time or the second period of time, wherein the trigger time window is substantially shorter than the first period of time;
maintain, responsive to the detection of the inspiration effort, a baseline pressure at the level in which the inspiration effort was detected by increasing the first period of time or the second period of time by a delay time so that the patient can complete the inspiration-exhalation cycle during the delay time prior to the switching event; and
switch the baseline pressure level after the delay time.

16. A non-transitory machine-readable medium comprising instructions stored therein, which when executed by a machine, cause the machine to perform operations, the machine-readable medium comprising:
instructions for supplying a breathing gas to the airway of a patient;
instructions for controlling a flow control valve and an exhalation valve of a ventilator for intermittently switching the airway pressure of the patient from a substantially constant high baseline pressure level to a substantially constant low baseline pressure and vice-versa such that the patient is able to breathe spontaneously within both a first period of time corresponding to the high baseline pressure level and a second period of time corresponding to the low baseline pressure level;
instructions for detecting an inspiration effort by the patient inside a trigger time window that immediately precedes a switching event of the intermittently switching the airway pressure at the end of the first period of time or the second period of time, wherein the trigger time window is substantially shorter than the first period of time;
instructions for controlling the flow control valve and the exhalation valve for maintaining a baseline pressure at the level in which the inspiration effort was detected by increasing the first period of time or the second period of time by a delay time so that the patient can complete the inspiration-exhalation cycle during the delay time prior to the switching event; and
instructions for controlling the flow control valve and the exhalation valve for switching the baseline pressure level after the delay time.

17. The machine-readable medium of claim 16, further comprising:
instructions for measuring expiratory flow from a beginning of exhalation inside the trigger time window;
instructions for comparing the measured expiratory flow to a preset level of flow trigger; and
instructions for switching a baseline pressure level after the delay time when the measured expired flow is equal or less than the preset level of flow trigger.

18. The machine-readable medium of claim 16, further comprising:
instructions for opening, inside the trigger time window at the substantially constant high baseline pressure level, the flow valve of the ventilator to sustain inspiration of the patient; and
instructions for simultaneously keeping the exhalation valve of the ventilator closed to maintain baseline pressure level at the substantially constant high baseline pressure level.

19. The machine-readable medium of claim 16, further comprising:
instructions for opening, inside the trigger time window at the substantially constant low baseline pressure level, the flow valve of the ventilator to sustain inspiration of the patient; and
instructions for simultaneously keeping the exhalation valve of the ventilator closed to maintain baseline pressure level at the substantially constant low baseline pressure level.

20. The machine-readable medium of claim 16, further comprising instructions for supplying a support pressure to the patient in a spontaneous breathing cycle, the support pressure being set in a Pressure Support Ventilation mode of the ventilator.

* * * * *